United States Patent [19]

Neubardt

[11] Patent Number: 5,196,015
[45] Date of Patent: Mar. 23, 1993

[54] PROCEDURE FOR SPINAL PEDICLE SCREW INSERTION

[76] Inventor: Seth L. Neubardt, 12 Shore Rd., Rye, N.Y. 10580

[21] Appl. No.: 876,861

[22] Filed: Apr. 30, 1992

[51] Int. Cl.$^5$ .............................................. A61B 17/56
[52] U.S. Cl. ........................................ 606/61; 606/72
[58] Field of Search ....................... 606/60, 61, 64, 65, 606/66, 67, 68, 72, 73, 74, 75, 76

[56] References Cited

U.S. PATENT DOCUMENTS

| | | | |
|---|---|---|---|
| 2,808,826 | 10/1957 | Reiner et al. | 128/2.1 |
| 3,892,232 | 7/1975 | Neufeld | 606/73 |
| 3,915,162 | 10/1975 | Miller | 606/73 |
| 4,175,555 | 11/1979 | Herbt | 606/73 |
| 4,450,835 | 5/1984 | Asnis | 606/73 |
| 4,461,300 | 7/1984 | Christensen | 128/419 |
| 4,463,753 | 8/1984 | Gustilo | 606/73 |
| 4,569,351 | 2/1986 | Tang | 128/419 |
| 4,824,433 | 4/1989 | März et al. | 604/21 |
| 4,907,577 | 3/1990 | Wu | 606/87 |

OTHER PUBLICATIONS

"The Adult Spine–Principles and Practice", vol. 2, Raven Press (1991), pp. 1928, 1935–1937, & 2035–2036.
H. N. Herkowitz, et al., "Instrumentation of the Lumbar Spine for Degenerative Disorders, Operative Techniques in Orthopaedics" (Jan. 1991), at 91–96.
"Anatomic Consideration for Sacral Screw Placement", S. Mirkovic, et al., *Spine*, 1991 supplement, at S289–S294.
"Surgical Anatomy of the Sacrum", S. I. Esses, et al., *Spine*, 1991 supplement, at S283 to S288.
"Complications of the Variable Screw Plate Pedicle Screw Fixation", J. L. West III, et al., Spine (May 1991) at pp. 576–579.

Letter of Charles D. Rosen, M. D., *Spine* (May 1991) at 599.
"Results of Spinal Arthrodesis with Pedical Screw--Plate Fixation", J. L. West, III, et al., *Journal of Bone and Joint Surgery*, Sep. 1991, at 1179–84.
"Internal Fixation of the Lumbar Spine with Pedicle Screw Plating", R. Roy-Camille, et al., *Clinical Orthopedics*, Feb. 1986, p. 7.
J. W. Simmons, MD, Surgical Technique Manual, published by Smith & Nephew Richards,Inc., pp. 4–11.
Instruction manual for the DUPACO Nerve Stimulator, model 5410 (Nov. 1983).

*Primary Examiner*—Robert A. Hafer
*Assistant Examiner*—Michael Brown
*Attorney, Agent, or Firm*—Leo Zucker

[57] ABSTRACT

Pedicle screws are inserted in spinal vertebrae in a manner to reduce the likelihood of nerve damage caused by improper screw placement. A screw opening is started in part of a skeletal region, e.g., a pedicle of a lumbar vertebra and an electric potential of a certain magnitude is applied to the inner surface of the opening while the patient is observed for nervous reactions such as leg twitching. The opening continues to be formed while the electric potential is applied until a desired hole depth is obtained in the absence of nervous reaction to the potential. The direction in which the screw opening is being formed is changed to a direction other than the last direction, after observing patient reactions to the electric potential when the screw opening was being formed in the last direction. A tool for carrying out the procedure includes a handle and a probe tip extending from the handle for forming an opening in bone tissue. Stimulator circuitry arranged inside the handle produces an electric potential of a predetermined level, and the potential is applied to the probe tip while the tool handle is manipulated to urge the probe tip into the bone tissue.

8 Claims, 3 Drawing Sheets

PROCEDURE FOR SPINAL PEDICLE SCREW INSERTION

BACKGROUND OF THE INVENTION

1. Field of the Invention

The present invention relates generally to a procedure for inserting pedicle screws into the spine as part of a spinal fixation instrument system, and particularly to a procedure whereby the likelihood of nerve damage caused by improperly placed pedicle screws can be reduced by implementing the present procedure with associated apparatus in situ.

2. Discussion of the Known Art

Instances arise when it becomes necessary to stabilize or fuse a portion of the spine from motion such as, for example, (1) after decompression wherein certain posterior spinal elements are removed to relieve pressure on neural elements, (2) after trauma or (3) because of the presence of tumors. Instrument systems that accomplish spinal fixation are known in the form of pedicle screws which are adapted to be inserted in selected vertebrae, and stiff rods or plates that connect adjacent pedicle screw heads to one another after the screws are inserted, thus resulting in the fixing or bracing of all vertebrae spanned by the rod or plate. Commercially available pedicle screws are usually made of stainless steel having overall diameters (including threads) ranging between 5.5 mm and 6.5 mm, and with lengths ranging between 25 mm and 55 mm.

The pedicles are the strongest parts of the spinal vertebrae and thus provide a secure foundation for the screws to which fixing rods or plates are attached. See R. Roy-Camille, et al, Internal Fixation of the Lumbar Spine With Pedicle Screw Plating, Clinical Orthopedics (Feb. 1986), at page 7; and H. N. Herkowitz, et al, Instrumentation of the Lumbar Spine for Degenerative Disorders, Operative Techniques in Orthopaedics (Jan. 1991), at page 91.

In order to derive the greatest mechanical integrity when anchoring pedicle screws in a spine fixing instrument system, it is therefore essential that the screws be guided and threaded in alignment with the pedicle axis and not be allowed to deviate off axis in which case the screw body or its threads will break through the vertebral cortex and impinge on or become dangerously close to surrounding nerve roots. A jig adapted for providing locations on the pedicles of a vertebra for insertion of pedicle screws, is disclosed in U.S. Pat. No. 4,907,577 (Mar. 13, 1990). The patent observes that the vertebral bodies will be fixed more stably the deeper the screws are inserted in the pedicle, and that slight deviations in the angle of screw insertion can injure nerve roots or the spinal cord.

Much appears in the literature with respect to the problems of misalignment of pedicle screws and the symptoms arising when the screws make contact with neural elements after breaking outside the pedicle cortex. Cutting into a nerve root or simply contacting the root gives rise to various postoperative symptoms such as dropped foot, neurological lesions, sensory deficits, or pain. The Adult Spine—Principles and Practice, Vol. II, at pages 1937 and 2035-36 (Raven Press 1991); J. L. West, et al, Complications of the Variable Screw Plate Pedicle Screw Fixation, Spine (May 1991), at 576-79; and J. L. West, et al, Results of Spinal Arthrodesis with Pedicle Screw-Plate Fixation, Journal of Bone and Joint Surgery (Sept. 1991), at 1182-83.

Apart from the jig of the mentioned '577 patent, no tools or devices are known with which pedicle screws can be guided or inserted into a vertebra in such a manner as to ensure that parts of the screws do not rupture the cortex and impinge on or come dangerously close to nerve roots. Current practice calls for the use of recognized landmarks along the spinal column for purposes of locating pedicle entry points, and the use of X-ray exposures or fluoroscopy to monitor the advancement of a metallic pedicle screw through the vertebra. But prolonged radiation exposure of the patient for purposes of proper screw placement is of course undesirable and this technique still has a misplacement rate of up to 21%. The Adult Spine—Principles and Practice, supra, at 2035. Nonetheless, a disturbingly high number of reported pedicle cortical disruptions has prompted one author to observe that "[a]lthough pedicle disruption does not necessary cause neural deficit, keeping the screw contained within the pedicle is one sure way to prevent it." The Adult Spine—Principles and Practice, supra, at 1937.

It is known generally that electrical potential pulses may be applied on or into the body of a patient for purposes of treatment. For example, U.S. Pat. No. 4,461,300 (Jul. 24, 1984) discloses a specially formed electrode for healing of bone or soft tissue fractures in a patient. The electrode has a lead wire connected at its back end, and is capable of being drilled or otherwise inserted into the patient's body with the lead wire in place.

It is also known that muscular reactions to electrical stimulation can be observed while a procedure is continued in accordance with the observed reactions. U.S. Pat. No. 2,808,826 (Oct. 8, 1957) shows electro-diagnostic apparatus and associated circuitry that act as a stimulator to measure the excitability of muscle or nerve tissue. A pair of electrodes are placed across a part of the patient's body and short duration pulses are applied with the pulse amplitude being slowly increased until a visible contraction appears. Electrical current readings are obtained for pulses of increasing duration, and a curve called a "strength-duration" curve is obtained, according to the patent. U.S. Pat. No. 4,824,433 (Apr. 25, 1989) discloses a puncturing and catheterizing device with a metal puncture needle and cannula suitable for puncturing nerve tracts. With the device connected to an electrical pulser, as long as the needle and surrounding cannula are inserted in the body through a nerve sheath, current pulses applied to the device induce visible motor reactions on body parts such as the hand. The visible reactions allow the physician to know that the puncture needle and cannula are being passed correctly along a space between a nerve and the nerve sheath.

Until applicant's invention, no technique, procedure or device was known that utilized visible motor reactions of a patient's limbs as a means for determining if a pedicle screw to be inserted in the patient's spine might impinge on or come in dangerously close proximity to a nerve root.

SUMMARY OF THE INVENTION

An object of the present invention is to overcome the above and other shortcomings in the prior art with respect to the location, placement and insertion of pedicle screws as part of a spine fixation instrument system in a patient.

Another object of the invention is to enable a surgeon to know, in situ, if a pedicle screw has (1) penetrated the cortex of a pedicle, (2) touched a nerve root, or (3) come in such close proximity to a nerve root as to require withdrawal and re-insertion of the screw.

A further object of the invention is to avoid the requirement of a new operation on a patient by ensuring that screw members stay contained within selected pedicles when a spine fixation instrument system is first applied in the patient.

Another object of the invention is to enable screw members forming part of an orthopaedic fixation instrument system to be inserted into a patient's bone tissue safely and without the requirement of continuous or frequent radiation exposure to ensure proper screw member alignment.

Yet another object of the invention is to reduce appreciably instances of postoperative complications such as dropped foot, neurological lesions, sensory deficits, or pain following surgery involving placement of screw members in a patient's spine.

According to the invention, a technique of inserting a screw member into bone tissue of a patient includes making an incision in the patient and exposing a skeletal region on which a bone fixation procedure is to be performed, locating an entry point on a part of the skeletal region in which a screw member of a fixation instrument system is to be inserted, and forming a screw opening in the skeletal region for insertion of the screw member using a determined direction for formation of the opening. The technique also includes applying an electric potential of a certain magnitude to the interior surface of the opening while observing the patient for nervous reactions to the electric potential, continuing the forming step and the applying step until a desired depth of the opening is attained in the absence of nervous reactions of the patient to the electric potential, and redirecting the formation of the screw opening in a direction other than a last determined direction after observing nervous reactions of the patient to the electric potential when forming the screw opening in the last determined direction.

According to another aspect of the invention, a surgical tool for forming an opening in bone tissue for insertion of a screw member, comprises a handle and a probe tip extending from the handle. The probe tip is adapted to form an opening in the bone tissue for insertion of a screw member. Stimulator circuit means associated with the handle produces an electric potential of a predetermined magnitude, and applies the potential to the probe tip while the handle is manipulated to urge the probe tip into the bone tissue.

For a better understanding of the present invention, together with other and further objects, reference is made to the following description taken in conjunction with the accompanying drawing, and the scope of the invention will be pointed out in the appended claims.

DETAILED DESCRIPTION OF THE INVENTION

Figure 1:
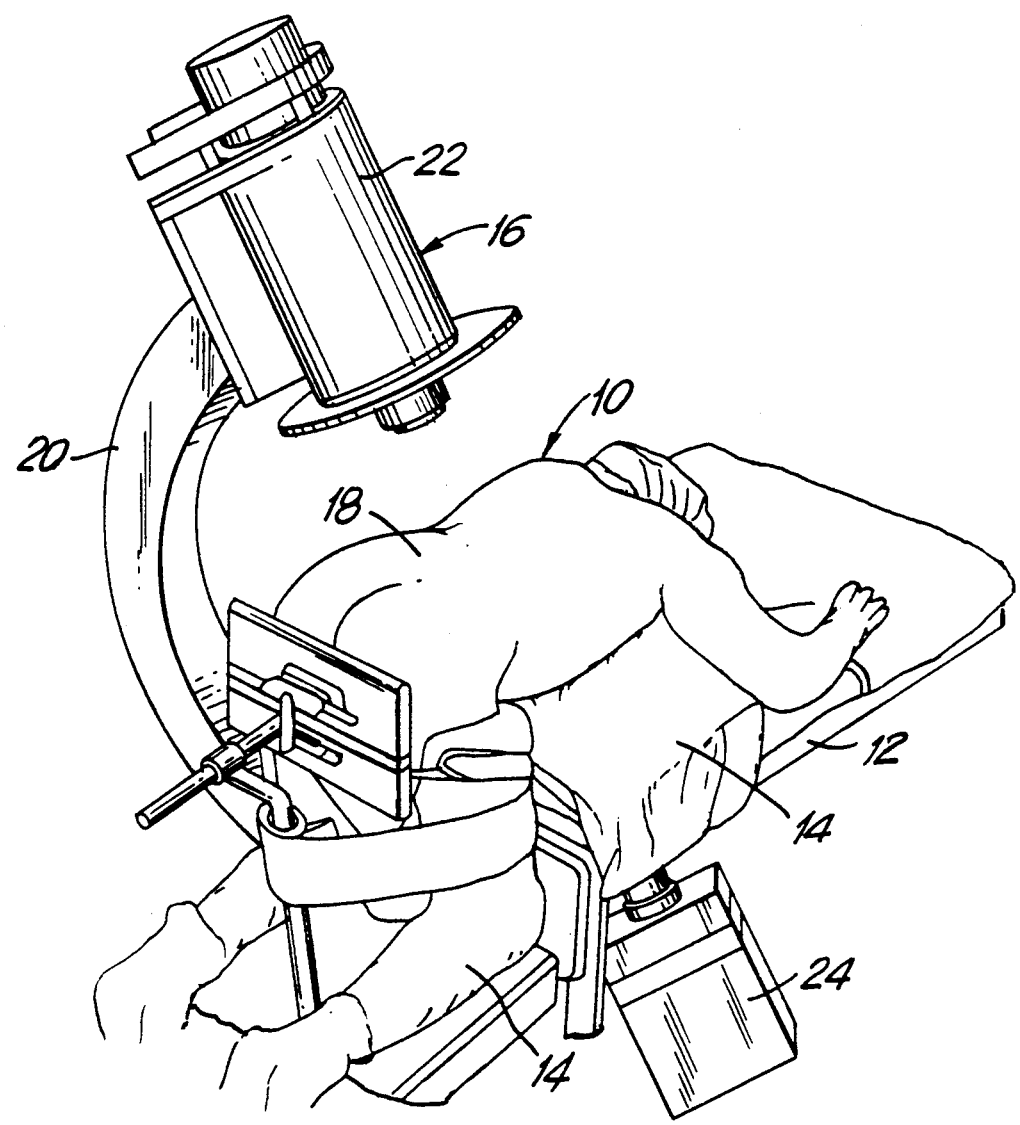
FIG. 1 is a view of a patient prepared to undergo lumbar fixation instrumentation surgery.

FIG. 1 is a view in an operating room showing a patient 10 lying prone on a spinal table 12. The patient's chest and groin are padded with suitable padding 14. In the illustrated example, the patient 10 is about to undergo lumbar fixation instrumentation surgery, thus making it preferable that the patient's abdomen hang free. The table 12 and padding material 14 should be substantially transparent to radiation from radiologic machinery 16 which is arranged to obtain exposures at various angles through the patient's lumber spinal region 18.

The radiologic machinery 16 is of the kind having a "C" arm 20 to permit rotation of an X-ray generating unit 22 at one end of the arm 20 together with an X-ray imaging unit 24 with which the generating unit 22 is aligned, so that the generating unit 22 and imaging unit 24 move in unison with one another as the C-arm 20 is positioned to expose a desired section in the patient 10.

Prior to making an incision, the lumbar region 18 is prepped and draped to maintain as much a sterile operating environment as is possible.

Figure 2:
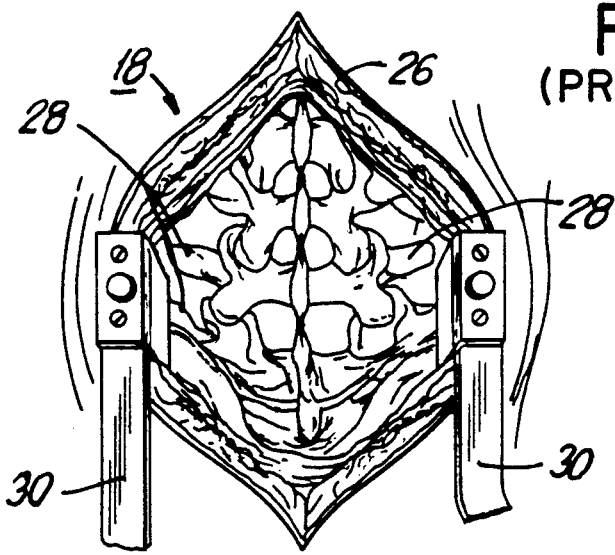
FIG. 2 is a view of a surgical field including a midline incision exposing a region of the patient's lumbar spinal region.

FIG. 2 is a view of a surgical field 26 as seen after a midline incision is made in the lumbar region 18 of interest. Tissue is dissected about the tips of the spinous processes, down to the tips of transverse processes 28 of the vertebrae to be fixed. Retractor arms 30 keep the surgical field 26 open sufficiently to allow the desired fixation instrumentation to be applied to the spine.

Figure 3:
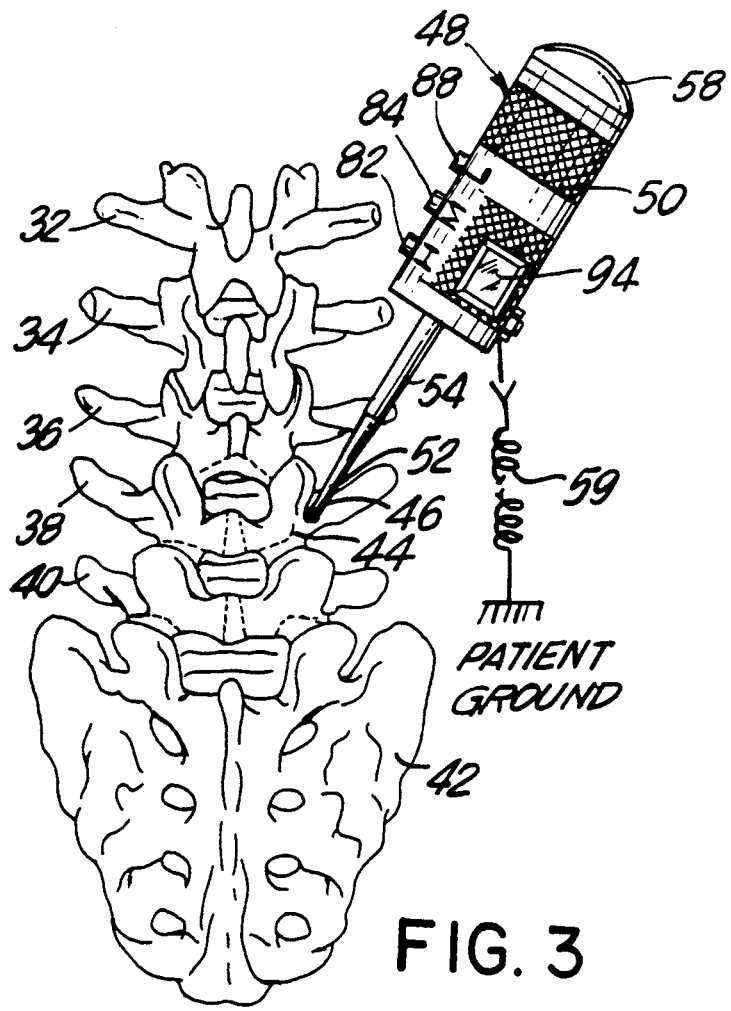
FIG. 3 is a posterior view of the lumbar spinal region and a tool for forming a pedicle screw opening according to the invention.

FIG. 3 is an enlarged posterior view of skeletal members of the lumbar spinal region 18 in the patient 10. The region includes a first lumbar vertebra 32 (L1), second lumbar vertebra 34 (L2), third lumbar vertebra 36 (L3), fourth lumbar vertebra 38 (L4), fifth lumbar vertebra 40 (L5), and sacrum 42 comprised of fused vertebrae S1-S5. Those vertebrae into which screw members are to be inserted are identified by the surgeon and pedicles, e.g., pedicle 44 of L4 vertebra 38, are probed for an entry point for the screw member.

Once an entrance point on the pedicle 44 is determined in accordance with surface landmarks or other known techniques (see H. N. Herkowitz, supra, at 93-94; and The Adult Spine, supra, at 1935), a screw opening is formed in the pedicle 44. The screw opening can be formed with a drill bit or probe, and once formed the opening may also be tapped if desired prior to insertion of a screw member.

Although the lumbar spinal region 18 of a patient is shown in the drawing for purposes of illustration, the present screw insertion procedure is not limited in application to the lumbar region of the patient 10, as will be appreciated by those skilled in the art.

In the present procedure, a screw opening 46 is formed in the pedicle 44 using a probe tool 48 having a stimulator/handle 50, a probe tip 52, and a tool shaft 54 connecting the tip 52 to the handle 50. Tip 52, the shaft 54 and the outer wall of the handle 50 may be made of stainless surgical steel or other suitable conductive metallic material of sufficient strength and which is capable of sterilization for repeated surgical use.

Before urging the tip 52 of the tool 48 into pedicle 44, it may be necessary first to remove cortical tissue with a high speed drill. The probe tip 52 is then located at the entrance point of the pedicle 44. A radiological image of the tip 52 at the entrance point on the pedicle 44 may be obtained with the machinery 16, although the present procedure does not require such imaging for proper screw insertion, as will be explained below. The screw opening 46 then continues to be formed with the tool 48 until the probe tip 52 attains a desired depth for the screw opening 46 in the pedicle 44 as may be verified by graduated marking indicia (not shown) on the tool shaft 54. If desired, an exposure with the radiologic machinery 16 can be made to confirm the tool depth.

Details of the construction of probe tool 48 are described in connection with FIG. 5.

Figure 5:
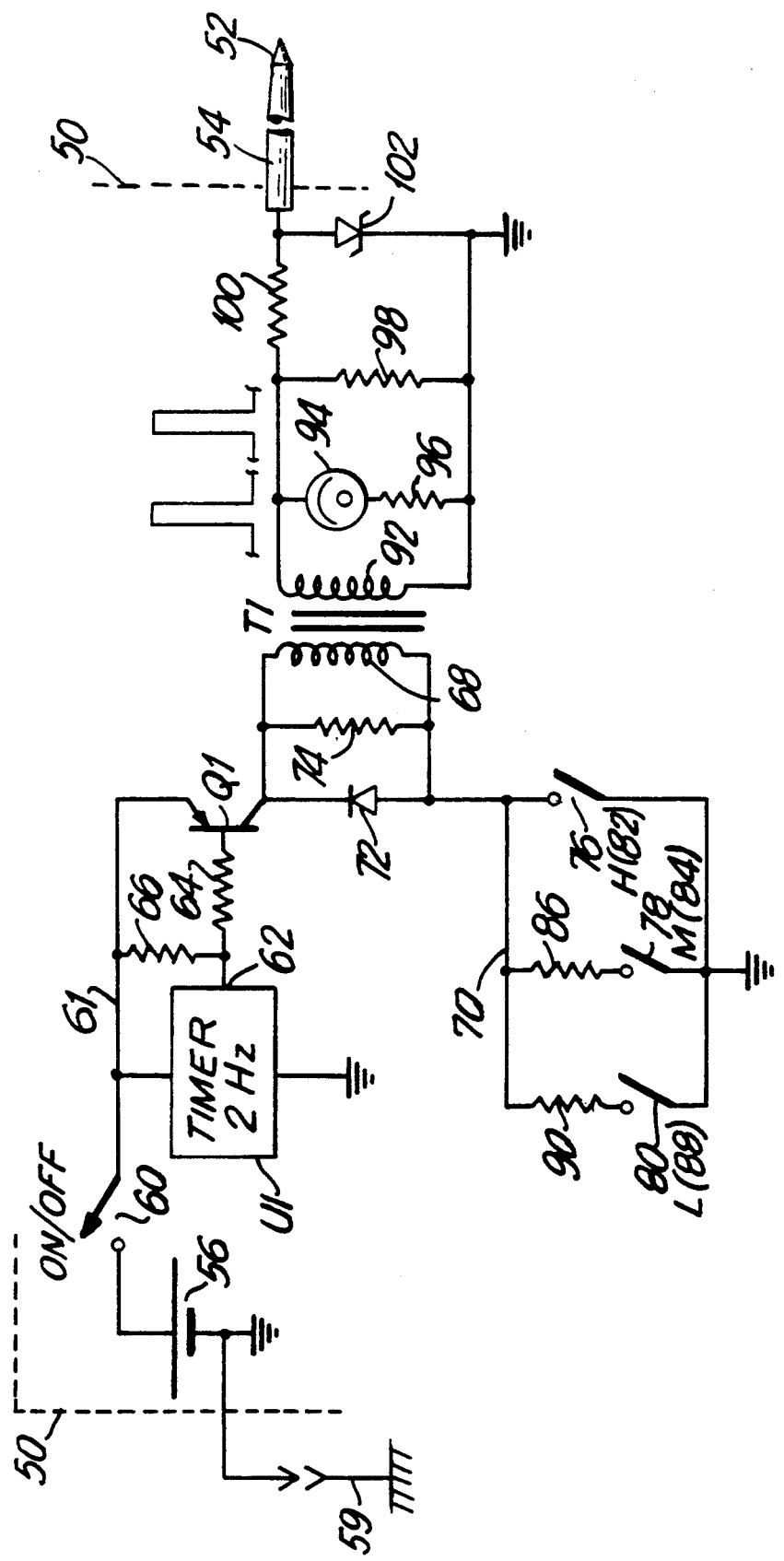
FIG. 5 is a schematic block diagram of components of a stimulator for carrying out the present procedure.

Inside the casing of stimulator/handle 50 there is arranged the nerve stimulator circuitry shown in FIG. 5. The stimulator circuitry is powered by a replaceable battery 56 which is accessible through a detachable handle cap 58 (FIG. 3). The battery 56 has its negative terminal grounded to the handle casing, and the positive terminal is switched to connect to the stimulator circuitry through a latching type ON/OFF switch 60 (not shown in FIG. 3). Switch 60 is preferably located at a lower part of the handle casing so as not to be inadvertently operated during use of the tool 48. The handle casing is connected to a patient ground such as muscle tissue within 6-8 cm from the surgical field, via a ground lead 59.

A conventional timer integrated circuit U1 such as device type 555 is connected to the switch 60 via supply voltage bus 61 to be powered by the battery 56 when the switch 60 is closed. The circuit U1 is set with appropriate external resistive and capacitive elements (not shown) to produce an output drive pulse at a repetition rate of about 2 Hz at timer output terminal 62. Output terminal 62 corresponds to terminal 3 of the mentioned type 555 timer IC.

A PNP current switching transistor Q1 has its base terminal connected to the output terminal 62 of timer U1 through a series resistor 64. An operating bias voltage level is set for transistor Q1 by bias resistor 66 connected between the timer output terminal 62 and the supply voltage bus 61. The emitter terminal of transistor Q1 is also connected to the supply bus 61.

A pulse current transformer T1 has one terminal of its primary winding 68 connected to the collector terminal of transistor Q1, and the other terminal of winding 68 is connected to a switch bus line 70. The cathode of a switching diode 72 and one terminal of a reverse current damping resistor 74 also connect to the collector of transistor Q1. The anode of the diode 72 and the other terminal of resistor 64 are connected to the switch bus line 70.

Three momentary SPST normally open push button switches 76, 78, and 80, each have one terminal connected to ground, i.e., the metal casing of the handle 50, respectively. Switch 76 corresponds to a high or H button 82 which protrudes through an opening in the handle casing as seen in FIG. 3. The other terminal of the switch 76 is connected to the switch bus line 70. Switch 78 corresponds to a medium or M button 84 protruding through the handle casing (FIG. 3), and has its other terminal connected to one terminal of a resistor 86. The other terminal of resistor 86 connects to the bus line 70. Switch 80 corresponds to a low or L button 88 also protruding through the handle casing (FIG. 3) and has its other terminal connected to a terminal of resistor 90. The other terminal of resistor 90 connects to the switch bus line 70.

Secondary winding 92 of the pulse transformer T1 is connected to a pulse output indicator lamp 94 through resistor 96. Winding 92 also connects across the terminals of a load resistor 98 one terminal of which is grounded, and the other terminal of which connects to one terminal of a current limiting resistor 100. The other terminal of the resistor 100 connects to the anode of Zener diode 102, and the cathode of diode 102 is grounded.

The shaft 54 of the probe tool 48 is connected to the anode of the Zener diode 102. Shaft 54 is electrically insulated by, e.g., epoxy resin or other strong electrically insulative material from the handle casing so that output stimulation pulses will not be "shorted" to ground through the tool handle 50.

With the switch 60 set to an ON state and the momentary switch 76 closed by depressing the switch push button 82, current of a certain magnitude is switched at a 2 Hz rate through the collector-emitter circuit of transistor Q1 in series with the transformer primary winding 68, by operation of the timer circuit U1. Transistor Q1 is biased by resistors 64 and 66 so as to induce relatively high (H) level voltage pulses across the secondary winding 92 of transformer T1 with switch 76 closed. For example, pulses having a peak voltage of about 80-100 or more volts may be induced across the secondary winding 92, and their presence observed via the indicator lamp 94. The Zener diode 102 may in fact comprise a number of Zener diodes connected in series so as to limit the peak pulse voltage that may be applied to a patient at the probe tip 52.

With only the switch 78 closed by depressing the push button 84, a medium (M) level voltage pulse is induced across the secondary winding 92 by limiting the amount of current switched by transistor Q1 through the primary winding 68. Resistor 86 is selected so that the medium level corresponds, for example, to a peak voltage of about 20 volts between the probe tip 52 and ground. This medium level voltage corresponds to a potential at which leg twitching would be induced if the pulses were applied in proximity to a nerve root as explained below.

When only the switch 80 is closed by depressing the push button 88 protruding from the tool handle casing, relatively low level voltage pulses are induced across the secondary winding 92 by further limiting the collector current through transistor Q1 via the resistor 90. The low level voltage pulses may, e.g., correspond to a peak voltage of about 4 volts between the probe tip 52 and ground. The low level voltage corresponds to a potential at which leg twitching would become observable if the pulses were applied directly on the nerve root.

In use, the surgeon applies the probe tip 52 at the entrance point of a pedicle into which a screw member is to be inserted, as mentioned above. The surgeon then urges the probe tip 52 into the pedicle 44 while holding the high or H level switch button 82 down and twisting the tool handle together with shaft 54 and tip 52 while urging the tool 48 in the direction of the pedicle axis. Administration of anesthesia has been tailored to allow muscle contraction in the patient for this stage of the surgery. As long as no twitching of the patient's leg is observed, the surgeon may continue to advance the probe tip 52 to the desired depth for the screw opening 46. If, however, twitching movement is observed, before advancing the probe tip further, the surgeon releases the H button 82 and depresses the medium (M) switch push button 84. If no twitching movement is observed, the surgeon continues to advance the tool with caution in the same direction. If, however, twitching movement continues to be observed, the surgeon then depresses the low (L) switch push button 88 to check for a nervous reaction. If none results, the surgeon may elect to continue in the same direction as previously, or to redirect the direction of the screw opening being formed through the pedicle. If a nervous twitch is observed even with only the low level switch 80 closed, the tool 48 should be withdrawn and a new pedicle screw opening 44 formed in a direction different from the last direction in which twitching movement resulted with only the low level pulses applied through the probe tip 52. Forming of the new screw opening proceeds as above with the surgeon urging the probe tip 52 in the different direction while depressing the H level button 82.

Figure 4:
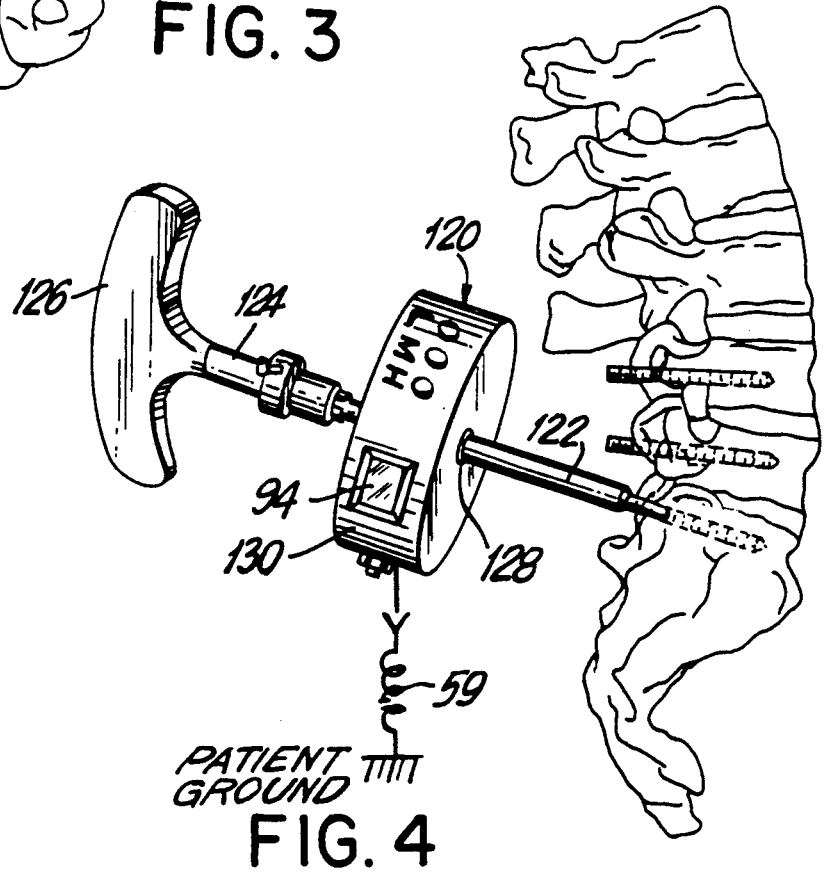
FIG. 4 is a lateral view of the lumbar spinal region and a pedicle screw driver tool according to the invention.

FIG. 4 shows a second embodiment of a probe tool 120 according to the invention.

The probe tool 120 is adapted to slide onto a shaft 122 of a commercially available tap or screw head driver 124. Specifically, the driver 124 has a handle 126 that is either nonconductive or is otherwise electrically insulated from shaft 122. The body of the probe tool 120 has a metallic sleeve 128 extending coaxially through the tool 120, and the sleeve 128 is arranged with set screws or other conventional locking means (not shown) to fit tightly on the shaft 122. The sleeve 128 is electrically insulated from an outer wall 130 of the tool body on which the three switch push buttons 82, 84 and 88 are accessible. The output indicator lamp 94 is also mounted on the wall 130. Electrical circuitry inside the tool 120 is identical to the stimulator circuitry disclosed above in connection with FIG. 5, except that the pulse output is applied to the conductive sleeve 128 rather than the tool shaft 54 of the probe tool 48 in FIG. 3. Accordingly, even after forming a screw hole with the tool 48 in FIG. 3, proper insertion of a pedicle screw can be ensured by placing the tool 120 in FIG. 4 over the metal shaft 122 of a tap or screw driver tool, grounding the wall 130 to the patient, turning the tool 120 on, and checking for patient reaction at each of the H, M and L levels of stimulation produced by the tool 120 while the tap or screw driver 124 is engaged with a tap or screw member head in the bone tissue. Again, if a patient reaction is observed even with the tool 120 set at the lowest stimulation level (L), the tap or screw member should be withdrawn and a new screw opening formed in a different direction using the probe tool 48 in FIG. 3.

EXAMPLE ONE

A "Digistim III" nerve stimulator made by Neuro Technology, Inc. of Houston, Tex., was set at a 2 Hz pulse rate and a pulse duration of 0.2 milliseconds. While a patient was undergoing lumbar spinal fixation surgery that required insertion of pedicle screws into the L5 vertebra, pulse amplitude output levels were determined at which the patient's leg would visibly twitch with the pulses applied (1) through the machine output leads, (2) through a so-called K-wire after insertion in the pedicle, and (3) through an inserted pedicle screw. One of the machine output leads was grounded to the patient through a needle inserted in muscle tissue near the surgical field.

It was discovered that when the ungrounded machine output lead was applied directly on a nerve root at the left side of vertebra L5, twitching occurred at a pulse level corresponding to a current setting of 1.5 ma. When the same lead was applied on the root at the right side of L5, the pulse level at which twitching was observed corresponded to a current setting of 2.4 ma. These current settings correspond to pulse voltage levels of 3.0 and 4.8 volts when a 2000 ohm load is connected to the output of the Digistim III.

Next, a "proximity" gap between the ungrounded machine lead and the nerve root including surrounding tissue at the left and the right sides of L5 was defined to be about 3 mm of the tissue between the lead tip and the nerve root. When in such proximity, pulse levels applied by the lead tip attained a value corresponding to a 5.0 ma current setting at which the patient's leg twitched with the lead at the left side of L5, and the pulse level needed for twitching with the lead at the right side of L5 corresponded to a current setting of 3.0 ma on the Digistim III unit.

A K-wire, about 0.062 inch diameter stainless steel and of the kind ordinarily used to form guide holes for pedicle screws, was drilled through the left pedicle cortex to a depth of about 45 mm on L5, and the stimulator unit output was connected to the wire. The pulse level needed to observe leg twitching corresponded to 15 ma. The pulse level for the right pedicle of L5 corresponded to 12 ma.

Finally, the K-wire was withdrawn and a screw member inserted in the left pedicle of L5. When the stimulator unit was adjusted for a pulse level corresponding to 44 ma, no twitching movement could be observed. For the right pedicle of L5, twitching was observed at the 44 ma setting.

EXAMPLE TWO

The stimulator unit used in EXAMPLE ONE was set for the same pulse rate and duration, and its output lead connected to 55 mm and 40 mm screws that were about to be inserted in a different patient's spine.

When the 55 mm screw touched the nerve root at the left side of L5, a pulse level corresponding to 12.9 ma was needed to produce twitching movement of the leg. When the stimulator unit output was applied through the 40 mm screw to the nerve root at the right side of L5, the threshold pulse level corresponded to a current setting of 9.8 ma.

With the screws properly inserted in the pedicles of L5, the pulse level had to be increased to a 71 ma setting to produce twitching movement, while no twitching movement could be induced with the stimulator unit lead connected to the screw inserted in the right pedicle of L5. A threshold pulse level corresponding to a 69 ma setting produced twitching when applied through the screw inserted in the right pedicle of L4.

EXAMPLE THREE

The Digistim nerve stimulator unit used in EXAMPLE ONE was set again to a pulse rate of 2 Hz and a pulse duration of 0.2 milliseconds. Data was obtained with a third patient who underwent lumbar spinal fixation surgery.

The stimulator unit lead was applied directly on the nerve roots at the left sides of L4 and L5, with the threshold pulse levels needed for leg twitching corresponding to current settings of 2.3 ma and 21 ma, respectively.

When a K-wire used to form a screw opening in the left pedicle of L5 was attached to the stimulator unit output, no twitching movement was observable up to a pulse level corresponding to a 41.5 ma setting. Similarly, with screws inserted in the left and the right pedicles of L5, no twitching movement was observable through pulse levels corresponding to a 80 ma setting on the Digistim III stimulator unit.

While the foregoing description represents preferred embodiments of the present invention, it will be obvious to those skilled in the art that various changes and modifications may be made without departing from the spirit and scope of the invention.

For example, the stimulator circuitry of FIG. 5 has been disclosed as contained within the probe tool 48 in FIG. 3 or inside the "slide on" tool 120 of FIG. 4. The stimulator circuitry of FIG. 5 may also be incorporated into the handle of a so-called sound probe used for sounding out screw holes for interior wall strength once the holes are formed. That is, although a formed screw hole may produce an acceptable sound when probed interiorly, the inside wall of the opening could nonetheless be dangerously close to a nerve root so that postoperative complications would probably ensue after a pedicle screw is inserted in the opening and fixation instrumentation is applied to the patient. According to the invention, applying nerve stimulation pulses during formation of a screw opening, as well as during the tapping and screw insertion phases of fixation surgery, ensures that screw members will be properly located and that postoperative complications arising from misdirected pedicle screws will be negated.

Accordingly, the present invention is to be delimited only in accordance with the following claims.

What is claimed is:

1. A technique of inserting a screw member into bone tissue, the screw member being part of a spinal fixation instrument system wherein rigid rods or plates are attached to heads of a number of screw members after insertion into adjacent parts of the bone tissue, said technique comprising the steps of:

making an incision in a patient and exposing a skeletal region for which region a bone fixation procedure is to be performed;

locating an entrance point on a part of the skeletal region into which part a screw member of a spinal fixation instrument system is to be inserted;

forming a screw opening in said part of the skeletal region for insertion of the screw member, using a determined direction for formation of the opening;

applying an electric potential of a certain magnitude to the inner surface of said opening while observing the patient for nervous reactions to said electric potential;

continuing said forming step and said applying step until a desired depth is attained for the screw opening in the absence of nervous reactions of the patient to said electric potential; and redirecting the formation of said screw opening in a direction other than a last determined direction after observing nervous reactions of the patient to said electric potential when forming the screw opening in the last determined direction.

2. The technique of claim 1, including observing twitching of a limb of the patient as a nervous reaction for initiating such redirecting step.

3. The technique of claim 1, including carrying out said forming and said applying steps substantially simultaneously using a single tool.

4. The technique of claim 3, including using a tool having a pointed probe tip for forming the screw opening.

5. The technique of claim 3, including using a tap driver tool for forming the screw opening.

6. The technique of claim 3, including using a screw head driver tool for forming the screw opening by driving a screw member into the bone tissue.

7. The technique of claim 1, including setting the magnitude of the electric potential in said applying step to a level at which nervous reactions are observed when the potential is applied in proximity to a nerve root adjacent the screw opening.

8. The technique of claim 1, including setting the magnitude of the electric potential in said applying step to a level at which nervous reactions are observed when the potential is applied on a nerve root adjacent the screw opening.

* * * * *